US008060377B2

(12) United States Patent
Dunham et al.

(10) Patent No.: US 8,060,377 B2
(45) Date of Patent: Nov. 15, 2011

(54) SYSTEM AND METHOD FOR COLLABORATIVE PATIENT CARE

(75) Inventors: Jamie Dunham, Winneconne, WI (US); Sue Peterson, Appleton, WI (US); Shana Hertzfeld, Appleton, WI (US); Judith Knox, Appleton, WI (US); Eileen Olson, Appleton, WI (US); Norma Turk, Appleton, WI (US); Kristine Vosters, Kaukauna, WI (US); Margaret Lauterbach, Appleton, WI (US); Beth Malchetske, Berlin, WI (US); James McGovern, Appleton, WI (US)

(73) Assignee: Thedacare, Inc., Appleton, WI (US)

( * ) Notice: Subject to any disclaimer, the term of this patent is extended or adjusted under 35 U.S.C. 154(b) by 477 days.

(21) Appl. No.: 11/856,709

(22) Filed: Sep. 17, 2007

(65) Prior Publication Data
US 2008/0183496 A1 Jul. 31, 2008

Related U.S. Application Data

(60) Provisional application No. 60/825,850, filed on Sep. 15, 2006.

(51) Int. Cl.
*G06Q 50/00* (2006.01)
(52) U.S. Cl. .................... 705/2; 705/3; 705/4; 600/300; 434/262
(58) Field of Classification Search .................. 434/262; 705/2, 3, 4; 600/300
See application file for complete search history.

(56) References Cited

U.S. PATENT DOCUMENTS

| 5,301,105 | A | * | 4/1994 | Cummings, Jr. | 705/2 |
|---|---|---|---|---|---|
| 6,177,940 | B1 | * | 1/2001 | Bond et al. | 434/262 |
| 7,299,192 | B2 | * | 11/2007 | Luttrell | 705/3 |
| 7,406,428 | B1 | * | 7/2008 | Havard | 705/4 |
| 2002/0128866 | A1 | * | 9/2002 | Goetzke et al. | 705/2 |
| 2002/0188182 | A1 | * | 12/2002 | Haines et al. | 600/300 |
| 2003/0014279 | A1 | * | 1/2003 | Roman et al. | 705/2 |
| 2003/0050801 | A1 | * | 3/2003 | Ries et al. | 705/2 |

OTHER PUBLICATIONS

Newswire article; Phillips with 2005 Technolody Leadership Award, Dec. 2005.*
Varian Systems introduces bew version of Eclipse advanced treatment planning software.*
Dialog Search History.*

* cited by examiner

*Primary Examiner* — Dilek Cobanoglu
(74) *Attorney, Agent, or Firm* — Alan R. Stewart; Godfrey & Kahn, S.C.

(57) ABSTRACT

A system for developing a patient care plan and executing the patient care plan and assessing the success of the planning and execution of the patient care plan. A coordinated, collaborative approach to the development of a patient care plan at the admission of a patient to a health care facility and may include a plurality of healthcare professionals in the development of the plan. The plan may include a plurality of phases spanning from admission through treatment and discharge of the patient from the health care facility. A system of executing the patient care plan with specific milestones established before transitioning the treatment from one stage of the care plan to the next stage of the care plan. A method of developing, executing and assessing the execution of a patient care plan including a plurality of phases of patient care and milestones to be met before transitioning to the next phase of care.

8 Claims, 16 Drawing Sheets

Care Objectives
Admission – Tollgate 1

| Type | Assessment / Reassessment | Interventions | Quality Measures | Goals | Psycho-social | Education | Disposition | Communication |
|---|---|---|---|---|---|---|---|---|
| 114 Symbol | ☺ | ☺ | ☺ | ☺ | ☺ | ☺ | ☺ | ☺ |
| 116 Action | Orientation | Height, weight, transfer PT to bed, assist to gown, vitials, ADLs, water, | | | | | | Tollgate planned and timed |
| | Arm bands | | | | | | | |
| | | Interventions: 02, IV, Blood Sugar, etc. | | | | | | |

FIG. 3

Tollgate 1

| Subjective patient information and documentation | Objective patient information and documentation | DC and LOS estimated | Ed folder with CRS handout, pen and pad of paper given to PT. PT able to state: "why I am here", "what's happening" |
|---|---|---|---|
| Patient Expectations/comfort index | Interventions established | Diagnostics Necessary interventions completed based on results | Continue to monitor and repeat labs as appropriate; Necessary interventions completed based on results |
| Med reconciliation initiated | Screens addressed: Immunization, Fall, DVT, Skin, Nutrition, Palliative, Abuse, Vent Bundle, Functional (Indicate NA for those not applicable | Goals/Milestones established | Quality Measures Identified |
| A. Consults called? B. Other disciplines notified: 1. if not order driven (ie Care Mgmt Pastoral Care and Dietary— communication order placed) Order driven departments-order is placed | Place holder | Collaboration with members of team, patient and family | Place holder |
| Disciplines Needs Identified | | | FIG. 4 |

Care Objectives
Tollgate 1 – Tollgate 2

| Type | Assessment / Reassessment | Interventions | Quality Measures | Goals | Psycho-social | Education | Disposition | Communication |
|---|---|---|---|---|---|---|---|---|
| Symbol | 😊 | 😊 | 😊 | 😊 | 😊 | 😊 | 😊 | 😊 |
| Action | Subjective PT reassessment | Interventions: activity, ADL's, | Risk Screenings | Goals / Milestones addressed | Needs Addressed | Documentation | Disposition | Coordination of care with ancillary dept. and |
|  | Objective PT reassessment | special needs, equipment, safety, diet, nutrittion, therapy, diagnosis, pain mgmt, isolation, | | Updated problem list as necessary | | | Acknowledge Orders | team members |
|  | | | | | | | | Consult rounding |
|  | | | | Written summaries of PT events | | | | MD rounding |
|  | | | | | | | | Therapies |
|  | | TLC | | | | | | Update PT & family/ contact person |
|  | | Environment, Safety Checks | | | | | | Care Team report/ shift |
|  | | | | | | | | Patient accuity |

FIG. 5

Tollgate 2

| Subjective patient improvement or stabilization achieved and documented | Objective patient information and documentation | Place Holder | Ongoing assessment of ed. Needs addressed<br>-ed. Implemented<br>teach back. |
|---|---|---|---|
| Patient Expectations/comfort index | Interventions addressed: Orders acknowledged, non-med treatments implemented or scheduled | Diagnostics<br>  Ordered<br>  Scheduled<br>  Necessary interventions completed based on results | Complete and monitor labs and repeat as appropriate<br>Necessary interventions completed based on results |
| Place Holder | Place Holder | Place Holder | Place Holder |
| Consults called?<br>Disciplines arrived that were urgently needed? | Essential Meds Given<br><br>Maintenance Meds Given | Update with patient and or family regarding plan of care status | Place holder |
| Disciplines Called/ Assessed | | | |

FIG. 6

Care Objectives
Tollgate 2 – Tollgate 3

| Type | Assessment / Reassessment | Interventions | Quality Measures | Goals | Psycho-social | Education | Disposition | Communication |
|---|---|---|---|---|---|---|---|---|
| Symbol |  |  |  |  |  |  |  |  |
| Action | Subjective PT reassessment | Interventions: activity, ADL's, special needs, equipment, safety, diet, nutrittion, therapy, diagnosis, pain mgmt, isolation, | Risk Screenings | Goals / Milestones addressed | Needs Addressed | Documentation | Disposition | Coordination of care with ancillary dept. and team members |
|  | Objective PT reassessment |  |  | Updated problem list as necessary |  |  | Acknowledge Orders | Consult rounding |
|  |  |  |  |  |  |  |  | MD rounding |
|  |  |  |  | Written summaries of PT events |  |  |  | Therapies |
|  |  |  |  |  |  |  |  | Update PT & family/ contact person |
|  |  | TLC |  |  |  |  |  | Care Team report/ shift |
|  |  | Environment, Safety Checks |  |  |  |  |  | Patient accuity |

FIG. 7

Tollgate 3

| | | | |
|---|---|---|---|
| Subjective patient improvement or stabilization achieved and documented | Objective patient improvement / physical reassessment completed and documented | Discharge needs Identified, addressed and date estimated | Ongoing assessment of ed. Needs addressed -ed. Implemented teach back. |
| Patient Expectations/comfort index | Interventions reassessed and progressed | Diagnostics<br>  Ordered<br>  Completed<br>  Resulted<br>  Necessary interventions completed based on results | Monitor and repeat labs as required<br>Necessary interventions completed based on results |
| Medication Reconciliation completed | Screens reassessed | Goals/Milestones | Open Quality Measures addressed |
| Consults notes available<br>Other Discipline treatment plan is on care plan | Essential meds given<br><br>Maintenance Meds given | Collaboration with patient and or family and members of care team | Place holder |
| Disciplines Assessment & evaluation | | | |

FIG. 8

Care Objectives
Tollgate 3 – Tollgate 4

| Type | Assessment / Reassessment | Interventions | Quality Measures | Goals | Psycho-social | Education | Disposition | Communication |
|---|---|---|---|---|---|---|---|---|
| Symbol | 😊 | 😊 | 😊 | 😊 | 😊 | 😊 | 😊 | 😊 |
| Action | Subjective PT reassessment | Interventions: activity, ADL's, special needs, equipment, safety, diet, nutrittion, therapy, diagnosis, pain mgmt, isolation, | Risk Screenings | Goals / Milestones addressed | Needs Addressed | Documentation | Discharge plan defined | Coordination of care with ancillary dept. and team members |
|  | Objective PT reassessment |  |  | Updated problem list as necessary |  |  | Acknowledge Orders | Consult rounding |
|  |  |  |  | Written summaries of PT events |  |  |  | MD rounding |
|  |  | TLC |  |  |  |  |  | Therapies |
|  |  |  |  |  |  |  |  | Update PT & family/ contact person |
|  |  | Environment, Safety Checks |  |  |  |  |  | Care Team report/ shift |
|  |  |  |  |  |  |  |  | Patient accuity |

FIG. 9

Tollgate 4

| Subjective patient improvement or stabilization achieved and documented | Objective patient improvement / physical reassessment completed and documented | Discharge needs Identified, addressed and date estimated | Ongoing assessment of ed. needs addressed<br>-ed implemented<br>-teach back |
|---|---|---|---|
| Patient Expectations/comfort index | Interventions reassessed and progressed | Diagnostics<br>Ordered<br>Completed<br>Resulted | Monitor and repeat labs as required<br>Necessary interventions completed based on results |
| Medication Reconciliation Completed | Screens reassessed | Goals/Milestones | Open Quality Measures addressed |
| Consults notes available and consultant discharge plan known<br>Other discipline discharge plan needs known and incorporated | Essential meds given<br><br>Maintenance meds given | Collaboration with patient and or family and members of care team | Anticipate<br>Follow up<br>accountability |
| Assure discipline, discharge plan defined | | | |

FIG. 10

Care Objectives
Tollgate 4 – Tollgate 5

| Type | Assessment / Reassessment | Interventions | Quality Measures | Goals | Psycho-social | Education | Disposition | Communication |
|---|---|---|---|---|---|---|---|---|
| Symbol | 😊 | 😊 | 😊 | 😊 | 😊 | 😊 | ⬤ | 😊 |
| Action | Subjective PT reassessment | Interventions: activity, ADL's, special needs, equipment, safety, diet, nutrittion, therapy, diagnosis, pain mgmt, isolation, | Risk Screenings | Goals / Milestones addressed | Needs Addressed | Documentation | Discharge plan defined | Coordination of care with ancillary dept. and team members |
|  | Objective PT reassessment |  |  | Updated problem list as necessary |  |  | Acknowledge Orders | Consult rounding |
|  |  |  |  | Written summaries of PT events |  |  |  | MD rounding |
|  |  | TLC |  |  |  |  |  | Therapies |
|  |  |  |  |  |  |  |  | Update PT & family/ contact person |
|  |  | Environment, Safety Checks |  |  |  |  |  | Care Team report/ shift |
|  |  |  |  |  |  |  |  | Patient accuity |

FIG. 11

Tollgate 5

| Place Holder | Clinical status stable | Discharge plan complete<br>Smoking Cessation completed if applicable | Ongoing assessment of needs<br>-final teach back with d/c letter and CRS as tool<br>-ed summary to next level of care |
|---|---|---|---|
| Patient Expectations/comfort index | Place Holder | Diagnostic<br>Completed<br>Resulted<br>Necessary interventions completed based on results | Labs<br>Resulted<br>Necessary interventions completed based on results |
| Discharge Medication Reconciliation and education Completed | | Goals/Milestones Met and follow up in place | Quality Measures Met |
| Ancillary departments notified | Administer vaccines if not completed earlier in stay (as appropriate) | Collaboration with patient and or family and members of care team | Follow up Accountability Assigned |
| Disciplines completed | | | |

Tollgate Form

| | | | |
|---|---|---|---|
| Date/Time of BCC | | | |
| Tollgate 1 time 6 hrs post care confr signature verifies tollgate check has been completed | Date/Time _____ Signature _____ | Date/Time _____ Signature _____ | Date/Time _____ Signature _____ |
| Tollgate 2 time 12 hrs post care conf signature verifies tollgate check has been completed | Date/Time _____ Signature _____ | Date/Time _____ Signature _____ | Date/Time _____ Signature _____ |
| I need input/recommendations from: *(154)* | ☐ ☐ | ☐ ☐ | ☐ ☐ |
| Admission status | Inpatient / Obs | Inpatient / Obs | Inpatient / Obs |
| Code Status | Full / No code / Partial | Full / No code / Partial | Full / No code / Partial |
| Milliman | day ___ of ___ | day ___ of ___ | day ___ of ___ |
| Interventions/ Needs for progression | ☐ ☐ ☐ ☐ ☐ ☐ | ☐ ☐ ☐ ☐ ☐ ☐ | ☐ ☐ ☐ ☐ ☐ ☐ |
| Subjective *(150)* | ☐ | ☐ | ☐ |
| Education (update plan of care) | ☐ ☐ | ☐ ☐ | ☐ ☐ |
| Medication | ☐ Med Rec completed<br>☐ Home meds reviewed<br>☐ _____<br>☐ _____<br>☐ _____ | ☐ Med Rec completed<br>☐ Home meds reviewed<br>☐ _____<br>☐ _____<br>☐ _____ | ☐ Med Rec completed<br>☐ Home meds reviewed<br>☐ _____<br>☐ _____<br>☐ _____ |
| Labs | C/R____ C/R____<br>C/R____ C/R____<br>C/R____ C/R____<br>C/R____ C/R____ | C/R____ C/R____<br>C/R____ C/R____<br>C/R____ C/R____<br>C/R____ C/R____ | C/R____ C/R____<br>C/R____ C/R____<br>C/R____ C/R____<br>C/R____ C/R____ |
| Diagnostic Tests | C/R____<br>C/R____<br>C/R____ | C/R____<br>C/R____<br>C/R____ | C/R____<br>C/R____<br>C/R____ |
| Consults | ☐<br>☐ | ☐<br>☐ | ☐<br>☐ |
| Risk Screens to be readdressed | ☐<br>Date/ Time due ____ | ☐<br>Date/ Time due ____ | ☐<br>Date/ Time due ____ |
| D/C Date, Needs, & Plans | Issues____<br>Date/Time____<br>Location____<br>Trans____<br>OOH DNR Band needed yes/no | Issues____<br>Date/Time____<br>Location____<br>Trans____<br>OOH DNR Band needed yes/no | Issues____<br>Date/Time____<br>Location____<br>Trans____<br>OOH DNR Band needed yes/no |
| MD called for | ☐ | ☐ | ☐ |

FIG. 14

| D/C Criteria | Does current criteria status meet D/C Goal Criteria? | | | | | |
|---|---|---|---|---|---|---|
| Neuro/cognition | Yes | No | Yes | No | Yes | No |
| Cardiac/Tele | Yes | No | Yes | No | Yes | No |
| Respiratory | Yes | No | Yes | No | Yes | No |
| Nutrition | Yes | No | Yes | No | Yes | No |
| GI | Yes | No | Yes | No | Yes | No |
| GU | Yes | No | Yes | No | Yes | No |
| Functional | Yes | No | Yes | No | Yes | No |
| Skin | Yes | No | Yes | No | Yes | No |
| IV | Yes | No | Yes | No | Yes | No |
| Pain | Yes | No | Yes | No | Yes | No |
| Glucose | Yes | No | Yes | No | Yes | No |
| Misc | Yes | No | Yes | No | Yes | No |

| Variance Tracking | | | |
|---|---|---|---|
| Date | Error (mistake, incorrect action, or omission) | Defect (The result of the mistake, incorrect action, or omission) | Corrective Action |
| | | | |
| | | | |
| | | | |
| | | | |
| | | | |
| | | | |

FIG. 15

Trial Tollgate Form — 254

Notes/HPI: Patient arrives with nausea/vomiting/dehydration (pt label)

| | | | |
|---|---|---|---|
| Date/Time of BCC | 1700 12/24/07 | 12/25 @1200 | |
| Tollgate 1 time<br>6 hrs post care conf<br>signature verifies tollgate check has been completed | 2300 12/24/07<br>Date/ Time<br>staff signature<br>Signature | 12/25 @ 1800<br>Date/ Time<br>staff signature<br>Signature | _____<br>Date/ Time<br>_____<br>Signature |
| Tollgate 2 time<br>12 hrs post care conf<br>signature verifies tollgate check has been completed | _____<br>Date/ Time<br>_____<br>Signature | 12/26 0000<br>Date/ Time<br>staff signature<br>Signature | _____<br>Date/ Time<br>_____<br>Signature |
| I need input/recommendations from... | ☐<br>☐ | ☐<br>☐ | ☐<br>☐ |
| Admission status | (Inpatient) / Obs | (Inpatient) / Obs | Inpatient / Obs |
| Code Status | Full / (No code) / Partial | Full / (No code) / Partial | Full / No code / Partial |
| Milliman | Gastroenteritis guideline day 1 of 2 | Gastroenteritis day 2 of 2 | day ___ of ___ |
| Interventions/ Needs for progression | ☑ without diarrhea<br>☑ enteric isolation<br>☑ ac and hs blood sugars<br>☑ nebs<br>☐<br>☐ | ☑ decreased loose stool<br>☑ ambulating<br>☑ isolation continue<br>☑ tolerating diet<br>☐<br>☐ | ☐<br>☐<br>☐<br>☐<br>☐<br>☐ |
| Subjective | ☐ without diarrhea | ☐ | ☐ |
| Education (update plan of care) | ☐ gastroenteritis A&P<br>☐ | ☐<br>☐ | ☐<br>☐ |
| Medication | ☑ Med Rec completed<br>☑ Home meds reviewed<br>☐<br>☐<br>☐ | ☑ Med Rec completed<br>☑ Home meds reviewed<br>☑ lactobacillus<br>☑ flagyl<br>☑ phenergan PRN | ☐ Med Rec completed<br>☐ Home meds reviewed<br>☐<br>☐ |
| Labs | (C/R) CBC C/R<br>(C/R) BMET C/R<br>C/R ___ C/R<br>C/R ___ C/R | (C/R) c-diff C/R<br>(C/R) stool cult C/R<br>C/R ___ C/R<br>C/R ___ C/R | C/R ___ C/R<br>C/R ___ C/R<br>C/R ___ C/R<br>C/R ___ C/R |
| Diagnostic Tests | C/R<br>C/R<br>C/R | C/R<br>C/R<br>C/R | C/R<br>C/R<br>C/R |
| Consults | ☐ poss. Speech therapy<br>☐ | ☑ speech therapy came<br>☐ | ☐<br>☐ |
| Risk Screens to be readdressed | ☑ done on admission<br>Date/ Time due ___ | ☐<br>Date/ Time due ___ | ☐<br>Date/ Time due ___ |
| D/C Date, Needs, & Plans | Issues ___<br>Date/Time 12/26<br>Location home<br>Trans son /auto<br>OOH DNR Band needed yes/no | Issues ___<br>Date/Time 12/25<br>Location home with son<br>Trans son/auto<br>OOH DNR Band needed yes/no | Issues ___<br>Date/Time ___<br>Location ___<br>Trans ___<br>OOH DNR Band needed yes/no |
| MD called for | ☐ | ☐ | ☐ |

| D/C Criteria | Does current criteria status meet D/C Goal Criteria? | | | | | |
|---|---|---|---|---|---|---|
| Neuro/cognition | (Yes) | No | Yes | No | Yes | No |
| Cardiac/Tele | (Yes) | No | Yes | No | Yes | No |
| Respiratory | (Yes) | No | Yes | No | Yes | No |
| Nutrition | Yes | (No) | Yes | No | Yes | No |
| GI | Yes | (No) | Yes | No | Yes | No |
| GU | (Yes) | No | Yes | No | Yes | No |
| Functional | (Yes) | No | Yes | No | Yes | No |
| Skin | (Yes) | No | Yes | No | Yes | No |
| IV | Yes | (No) | Yes | No | Yes | No |
| Pain | Yes | (No) | Yes | No | Yes | No |
| Glucose | Yes | (No) | Yes | No | Yes | No |
| Misc. | Yes | No | Yes | No | Yes | No |

| Variance Tracking | | | |
|---|---|---|---|
| Date | Error (mistake, incorrect action, or omission) | Defect (The result of the mistake, incorrect action, or omission) | Corrective Action |
| 8/20/2007 | ED did not start Antibx within time window | Quality Metric Failure | Tracked on pneumonia bndle board for bundle manager to work with ED for RCA |
| 8/20/2007 | Delay in transc. For exr (not within 8 hour TAT) | Unable to provide result to provider for treatment plan | Called Transc. - Prioritized result in pool. Notified Supervisor of tracking board to vist GEMBA visit this week. |
| | | | |
| | | | |
| | | | |
| | | | |

US 8,060,377 B2

SYSTEM AND METHOD FOR COLLABORATIVE PATIENT CARE

CROSS-REFERENCE TO RELATED APPLICATION

The present application claims benefit of priority to earlier filed provisional application, U.S. Application Ser. No. 60/825,850, filed on Sep. 15, 2006, the disclosure of which is incorporated herein by reference.

BACKGROUND

In the health care industry, there are a number of professionals who provide services and care to patients who may be admitted to a care facility, such as a hospital. Because each of these professions has a unique set of skills and training, and unique sets of standards regarding care and treatment, crafting a common plan for the overall treatment and care of a patient can sometimes be problematic. The lack of a common and coherent plan for treatment of a patient can result in diminished confidence in the patient and their family in the course of treatment and a lack of efficiency in providing care and treatment.

That lack of efficiency in the treatment plan and the provision of treatment can lead to increased stays in hospital and also to increased costs and disruption of service to other patients.

In conventional medical practice, multiple treatment or care plans may be written for each patient. However, conventionally, these plans are not developed at the same time and based on the information from the patient. It is this lack of commonality and coherence between the different treatment or care plans that the present disclosure seeks to address.

It has been noted in statistical research regarding the quality and efficacy of health care in the U.S. that as many as 98,000 people die in U.S. hospitals each year as a result of errors. Further, it is estimated that as many as sixty-five patients out of every one thousand patients treated may suffer injury or illness as a consequence of their treatment. These statistics point to a need to improve the provision of health care provided in a hospital or health care facility setting.

Improvements to the planning and execution of patient care plans are desirable.

SUMMARY

The present disclosure relates generally to improvements in the establishment of patient care plans and the execution of patient care plans. More specifically, the present disclosure relates to a coordinated, collaborative approach to the development of a patient care plan at the admission of a patient to hospital and may include a plurality of healthcare professionals in the development of the plan. The present disclosure also relates to an approach to executing the patient care plan during the patient's stay in hospital with specific milestones established before transitioning the treatment from one stage of the care plan to the next stage of the care plan.

BRIEF DESCRIPTION OF THE DRAWINGS

FIG. 3 is a list of care objectives to be met for a patient at a first tollgate of a patient care plan developed according to the present disclosure.

FIG. 4 is a listing of elements to be addressed in the first tollgate corresponding to the objectives of FIG. 3.

FIG. 5 is a listing of care objectives to be met for the patient between the first tollgate of FIG. 4 and a second tollgate of the patient care plan developed according to the present disclosure.

FIG. 6 is a listing of elements to be addressed in the second tollgate corresponding to the objectives of FIG. 5.

FIG. 7 is a listing of care objectives to be met for the patient between the second tollgate of FIG. 6 and a third tollgate of the patient care plan developed according to the present disclosure.

FIG. 8 is a listing of elements to be addressed in the third tollgate corresponding to the objectives of FIG. 7.

FIG. 9 is a listing of care objectives to be met for the patient between the third tollgate of FIG. 8 and a fourth tollgate of the patient care plan developed according to the present disclosure.

FIG. 10 is a listing of elements to be addressed in the fourth tollgate corresponding to the objectives of FIG. 9.

FIG. 11 is a listing of care objectives to be met for the patient between the fourth tollgate of FIG. 10 and a fifth tollgate of the patient care plan developed according to the present disclosure.

FIG. 12 is a listing of elements to be addressed in the fifth tollgate corresponding to the objectives of FIG. 11.

FIG. 13 is a first page of a tollgate form corresponding to the care objectives for transitioning between a second tollgate of a patient care plan according to the present disclosure and a third tollgate of the patient care plan.

FIG. 14 is a second page of the tollgate form of FIG. 13.

FIG. 15 is a second embodiment of the first page of the tollgate form of FIG. 13, with entries on the form corresponding to a plurality of phases of a patient care plan according to the present disclosure.

FIG. 16 is a second embodiment of the second page of the tollgate form of FIG. 14, with entries on the form corresponding to the first page of the form shown in FIG. 15.

DETAILED DESCRIPTION

Figure 1:
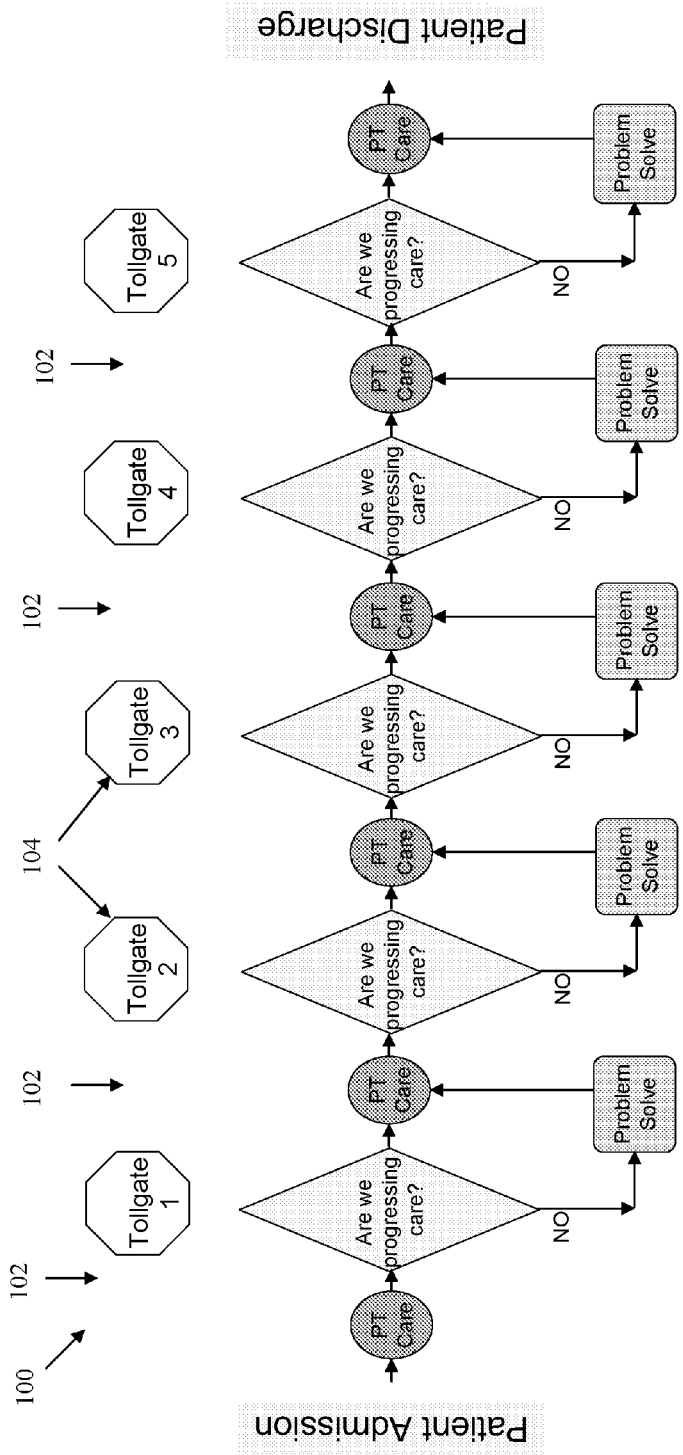
FIG. 1 is a diagram of an overall patient care plan structure according to the present disclosure.

During the intake and admittance process for a new patient at a hospital, it is not unusual for a variety of health care professionals and administrative staff to interview the patient and/or their family. While many of the questions asked during the interview process are vital to assessing the patient's condition and gathering information that will aid the treatment of the patient, many of the questions asked are also duplicative. Much of this duplication of effort comes from the fact that the different health care professionals need similar information to formulate a care plan for the patient. The reason for the duplicate questions comes from the fact that the different professionals visit with the patient at different times during the intake process and the information gathered by each professional is typically not available to the other professionals in a timely fashion. Often the same information may have been gathered by a care professional but has not been captured or recorded in any tangible medium that will allow sharing of the information with other professionals.

Another implication of the conventional approach to patient intake and diagnosis is that the intake process is stretched out over time. Each of the professionals need to visit with the patient prior to the professional being able to formulate a patient care plan and the contents of the different plan will likely have some dependency or overlap with the other care plans. Coordination during the assessment between the different professionals can be time-consuming and completion of the plans may be a precursor to the patient being fully admitted into the hospital and treatment begun.

The present disclosure contemplates a team of professionals representing each of the stakeholder professions involved with the development of a comprehensive patient care plan during the admission process. The team of professionals, including for example but not limited to, a physician, a nurse and a pharmacist, would be jointly involved in the information gathering and assessment of the patient. Rather than different professionals being involved at different times, this team would be together, examining, gathering information and questioning the patient contemporaneously. Questions called for or implicated in the development of different elements of the comprehensive patient care plan are asked once and the information required by each professional is gleaned from one answer from the patient or the family. In the interest of preserving patient privacy while still ensuring the commonality of the process for all professionals, one or more of the involved care professionals may be visually shielded from the patient but able to hear and participate verbally in the examination and information gathering. Such a shielded professional, such as, for example, a pharmacist, may be able to aid a physician in the determination of a pharmacological plan and will hear the medications orders directly from the physician. This will remove delay in the med orders being placed and the treatment being initiated.

This also ensures that each professional is hearing the same information. It is not uncommon for patients to respond differently to the same general question asked by different professionals. In the conventional approach, the different answers could lead to confusion or lack of coherence in the different professionals' care plans and these discrepancies must be addressed at a later time, when and if the care plans come into some degree of conflict with each other. This may result in delays or problems in timing or consistency of the care provided based on the different plans. Having each professional hear the answer simultaneously, these potential discrepancies can be identified and addressed before they can have an adverse effect on the diagnosis and treatment of the patient.

By having the professionals work together to examine, question and gather information regarding the patient, the process of developing a specific patient care plan can also be streamlined. Instead of having each professional develop an individual plan, and then having to harmonize the different plans at some later point in time, the professionals who have gathered the relevant information may work together to build a single coherent plan from the outset. No additional time or resources will need to be expended to ensure that the elements of the plans related to the different professionals mesh together. The different elements may be formulated jointly and in cooperation with each other.

One additional added benefit of the joint development of the patient care plan elements is that the time required to establish the plan and then begin to implement the plan may be shortened rather dramatically. It may not be uncommon for conventional independent intake procedures to require a number of hours from entry of a non-critical care patient into the hospital until the care plan is in place and treatment can begin. According to the present disclosure, the time required to analyze a patient's needs, development the care plan and initiate treatment may be shortened to a maximum time of ninety minutes.

While the present disclosure is generally focused on non-critical patient intake, efficiency and coherence improvements inherent in the described approach may also be extended to critical emergency patient intake. In emergency time-sensitive situations, such as for example, trauma center patient intake, it is more common to have a team of professionals treating the patient from the time of entry. However, improvements of the present disclosure may be applied to the development of an overall patient care plan for the course of a patient's stay in hospital, beyond the critical response phase in the trauma center or emergency room. Features of the present disclosure may also be incorporated into the emergency patient intake process to aid what may be currently an interdisciplinary or interprofessional treatment team approach to help improve the efficiency of these more time sensitive operations. In addition, after the critical treatment phase has been completed, the process of the present disclosure may then also be applied to develop the overall care plan for the patient.

In addition to improving the efficiency and coherence of the intake and patient care plan development processes, the present disclosure also relates to the structure and implementation of the care plan over the course of the patient's stay in hospital and after discharge. As shown conceptually in FIG. 1, the care plan 100 may have a plurality of phases 102 of treatment beginning with the entry of the patient into the hospital.

As shown in FIG. 1, each phase 102 of care plan 100 is linearly arranged and dependencies between the different phases may be coordinated so that no two phases 102 are in the process of being executed simultaneously. This may help ensure that there is no confusion within the care plan as to which of several treatments or actions should precede or follow other treatments or actions. The care plan may be developed so that there is no temporal or treatment overlap between and among phases, requiring each phase 102 to be completed and certified completed by a milestone or tollgate 104 before the next phase 102 may begin. The contents of each phase 102 may be controlled so that if several treatment elements need to take place simultaneously, these elements are all in the same phase 102 and the phase includes information as to the order in which the treatments should be performed or the extent of overlap of or between treatments.

Figure 2:
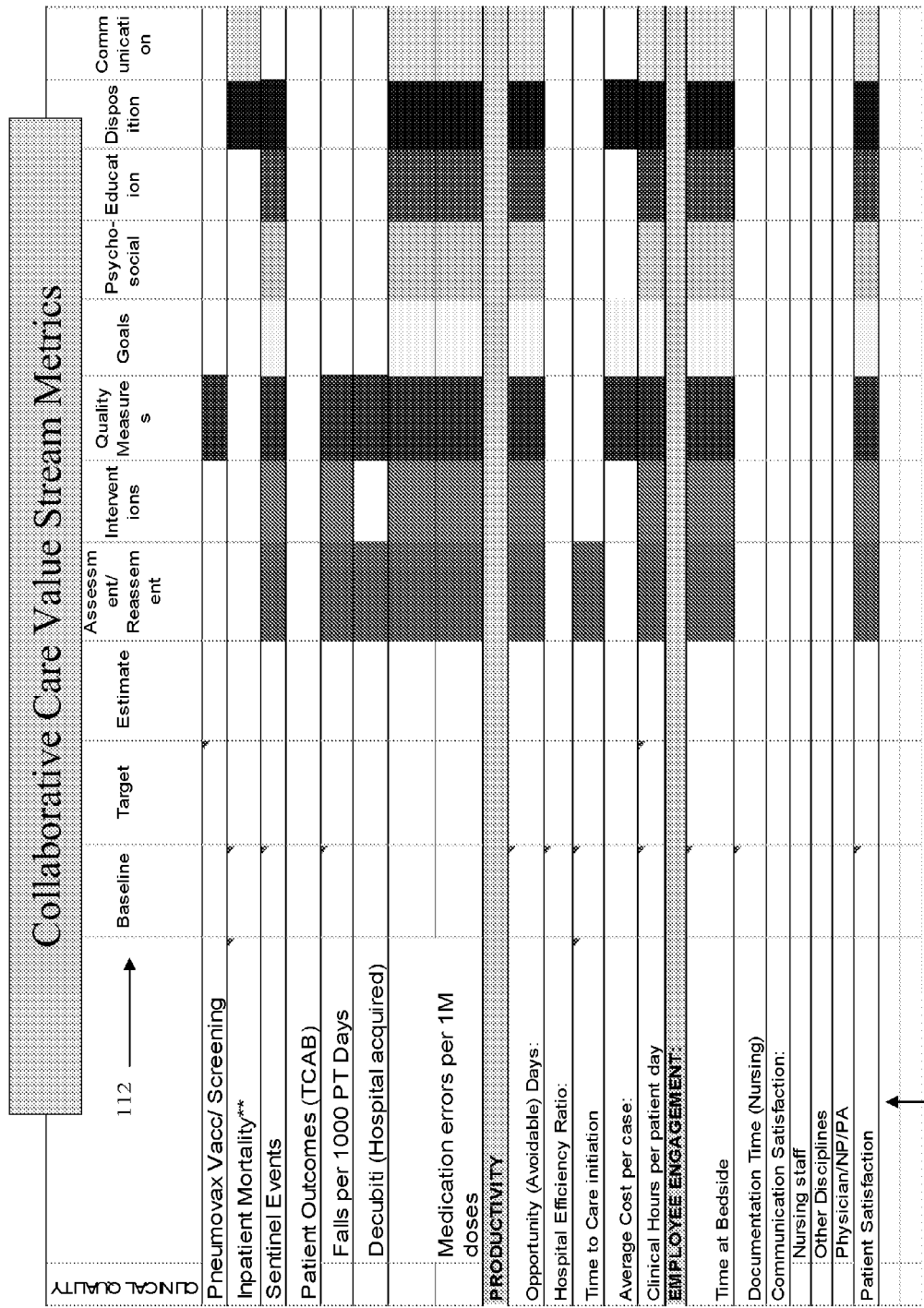
FIG. 2 is a table of metrics and categories of improvement that may be addressed by the patient care plan of FIG. 1.

FIG. 2 is a table which illustrates a plurality of metrics 110 that may be used to evaluate the need for and the effectiveness of a collaborative care approach as disclosed herein. Each of the metrics 110 listed on the left side of the table are further categorized as indicated in the right side of the table. The table includes shading illustrating for which of a plurality of categories 112 (listed along the top of the table) the metrics might be measured or recorded. As is shown, many of the metrics 110 used indicate effects throughout the various categories 112 listed, so that improvement of these metrics are indicative a broad efficacy of the collaborative care approach disclosed herein.

FIG. 3 illustrates a list of example care objectives that may be addressed in the care phase extending from admission of a patient to a health care facility up to the review of Tollgate 1, relating to the completion of the admission process of the patient to the care facility and establishment of the care plan. The shading of the symbols within symbol row 114 indicates to which of the categories 112 of FIG. 2 that these care objectives may be related. Under one or more of the categories 112 is a list of actions 116 that may be included in the services or activities 116 that may be included in this process.

As an example, this phase of care may be defined as actions that must take place within the first ninety minutes that a patient is in the care facility.

FIG. 4 illustrates the elements that may be included in Tollgate 1, which may be used to signal the completion of the admissions process and the development and initiation of the care plan for a particular patient. Within each of the Tollgate elements are an identifier of the category from FIG. 2 to which each of the elements relates. The elements that mat be included in this Tollgate may be different and adapted to the care plan for each patient. Once the elements for Tollgate 1 (and for any future Tollgates described below) are defined, the elements become requirements which must be achieved before the patient care plan is permitted to advance to the succeeding phases of care. As noted above, these objectives to be completed by the close of the first care phase and the tollgate may preferably be completed and passed within the first ninety minutes.

FIG. 5 illustrates a list of example care objectives that may be addressed in the care phase between Tollgate 1 and Tollgate 2. The color codes of the symbols indicate to which of the categories of FIG. 2 that these care objectives may be related. Actions are again included is list form beneath one or more of the listed categories. This care phase may preferably span, for example, the first four hours that the patient is in the care facility, and following the completion of Tollgate 1.

FIG. 6 illustrates the elements that may be included in Tollgate 2. Within each of the Tollgate elements are an identifier of the category from FIG. 2 to which each of the elements relates. As noted above, the objectives of Tollgate 2 may preferably be completed within the first four hours and after the completion of Tollgate 1.

FIG. 7 illustrates a list of example care objectives that may be addressed in the care phase between Tollgate 2 and Tollgate 3. The color codes of the symbols indicate to which of the categories of FIG. 2 that these care objectives may be related. This care phase may preferably span, for example, the first twenty-four hours that the patient is in the care facility, and following the completion of Tollgate 2.

FIG. 8 illustrates the elements that may be included in Tollgate 3. Within each of the Tollgate elements are an identifier of the category from FIG. 2 to which each of the elements relates. As noted above, the objectives of Tollgate 3 may preferably be completed within the first twenty-four hours and after the completion of Tollgate 2.

FIG. 9 illustrates a list of example care objectives that may be addressed in the care phase between Tollgate 3 and Tollgate 4. The color codes of the symbols indicate to which of the categories of FIG. 2 that these care objectives may be related. This phase of care may preferably extend up to approximately twenty-four hours prior to discharge of the patient from the care facility.

FIG. 10 illustrates the elements that may be included in Tollgate 4. Within each of the Tollgate elements are an identifier of the category from FIG. 2 to which each of the elements relates. As noted above, the objectives of Tollgate 4 may preferably be completed within the twenty-four hours of the discharge of the patient from the care facility and after the completion of Tollgate 3.

FIG. 11 illustrates a list of example care objectives that may be addressed in the care phase between Tollgate 4 and Tollgate 5. The color codes of the symbols indicate to which of the categories of FIG. 2 that these care objectives may be related. This phase of care may preferably extend from approximately twenty-four hours prior to discharge of the patient from the care facility up to the discharge of the patient.

FIG. 12 illustrates the elements that may be included in Tollgate 5. Within each of the Tollgate elements are an identifier of the category from FIG. 2 to which each of the elements relates. As noted above, the objectives of Tollgate 5 may preferably be completed within two hours prior to the discharge of the patient from the care facility and after the completion of Tollgate 4.

Referring now to FIGS. 13 and 14, a first page 150 and a second page 152 of a tollgate form 154 are illustrated that may be used by one or members of the patient care team to assess and determine the status of the actions and objections set for a patient at a particular tollgate during the process of carrying out the patient care plan. The particular example of tollgate form 154 may be used at the conclusion of up to three phases of treatment in the plan illustrated above. The form of FIGS. 13 and 14 may be a hardcopy form, such as printed on paper, or it may be embodied in a digital format, such as displayed on a desktop or laptop computer screen, or on a palm-style or other tablet type computing and/or data capture device. If it is a paper or other hardcopy form, it may be a print from a digital record of the patient care plan that has been generated or printed to facilitate bedside or conference room data collection and recordation. On second page 152 is a table for listing any issues with the creation or the execution of the patient care plan that may be used as feedback to assist the treatment of future patients.

Referring now also FIGS. 15 and 16, a sample form 254 is shown which has been filled out in accordance with a particular patient care plan and has been used to address the elements of a plurality of tollgates in this plan.

The elements within each care phase and each tollgate are indicated above as illustrative examples and not intended to limit the nature and extent of elements that might be included. The basis for the selection of elements is preferably medical need and administrative requirements, although other bases may also be used to drive the selection of the elements. It is intended that any items or elements listed in either a care phase or a tollgate as part of the overall care plan for a patient will be directly related to the provision of services to the patient and/or the patient's family.

While the care plan as described herein includes five distinct care phases with five corresponding tollgates, the number of tollgates and care phases may be adapted as needed for a particular care facility or for the care of a particular patient or group of patients. With particular diagnoses, more or fewer phases and corresponding tollgates may be defined. Longer term care facilities and patients with longer term care needs and in-hospital stay requirements may have many more care elements, phases and tollgates. Out-patient centers and non-critical care facilities may admit, treat and discharge patients on a much shorter time scale than described above and the number and timing of phases and corresponding tollgates may be adapted for these different time scales and care requirements. Full spectrum care facilities including, for example, critical care departments, Level 1 Trauma Centers, oncology treatment facilities, etc, may have a plurality of different implementations of the collaborative patient care plan described herein that have been adapted to meet the particular needs of different groups patients and health care providers.

The above described care plan is configured to work with an average hospital stay of four days. The stakeholder care providers involved in the treatment of a patient will determine the appropriate planning timeframe for a care plan while the care is being developed. The overall length of the plan, the number of tollgates, the elements to be included in each care phase and the desired outcome are all defined during the initial evaluation period described above. If the anticipated stay is only two days, based on the initial diagnosis, the plan would be adapted to match the length of stay and the course of treatment called for by the diagnosis and the patient's particular characteristics. It is anticipated that the care planning process described above is a flexible and adaptive model. By this, it is meant that the plan may be set initially to match the apparent patient conditions and diagnosis, but the care phases, elements within the phases and the tollgates may be altered to match changing requirements of the patient or changes to the initial diagnosis. For example, new symptoms may appear during the course of treatment or patient condition may be altered unexpectedly during treatment. The care plan may be adapted as needed to address these changed conditions or symptoms.

It is anticipated that the overall approach described above may be adapted as needed to address particular patients or groups of patients, different health care providers or groups of providers, and for different health care facilities or groups of facilities. The collaborative care plan described above may be implemented as a system and the system may be automated and computerized for use by the care providers within a particular facility or organization. In such an automated system, the patient care planning, execution and tracking according to the present disclosure may be recorded as electronic signals of some form of digital storage medium. However, it is anticipated that such a system may be implemented without the need for automation. In other words, a system of patient care planning, execution and tracking may be accomplished in a series of hardcopy documents.

A test implementation of a patient care planning system according to the present disclosure was carried out at a unit of an existing health care facility. Prior to the initiation of this test implementation, a series of benchmarks for performance measures were established regarding the current operation of the facility. Over the course of several months, the patient care planning system was used to plan and execute the provision of care to patients assigned the unit during their in-patient stays at the facility. As the test implementation was progressing, the same performance measures were continually addressed to determine variations from the original benchmarks. The changes to the performance measures from the benchmarks in a positive direction provided validation of the approach described herein.

In the test implementation, the performance measures included such things as patient satisfaction (subjective), quality improvements related to medication reconciliation expressed in terms of the overall number of errors per patient, quality performance core measures specific to patient care quality, length of stay and overall patient cost for treatment. With regard to patient satisfaction, the test unit of the facility noted an increase of approximately 24% above the benchmark. The overall length of stay on average was reduced by approximately 34% over the course of the first six months of operation of the unit. An overall reduction of approximately 40% in the cost to the patient of the care received was also realized over this same period of time.

Of particular note is the reduction of the average number of errors per patient in the medication reconciliation and the improvement to the quality performance core measures that were achieved by the unit over the first six months of operation. The medication reconciliation measure relates to any medication errors that might be made during the course of a patient stay. Over the first six months of operation of the test implementation, the medication reconciliation error rate per patient was reduced by almost 100%. For several of the months of operation, zero errors total occurred in the unit.

With regard to the core measures, there are several elements or bundles which are measured to derive an overall performance rate. For two particular measures, pneumonia and congestive heart failure, significant improvements have also been realized. For the core measure relating to pneumonia, compliance went from approximately 38% to approximately 98.4%, with five of the six months demonstrating 100% compliance with the core measure. For the core measure relating to congestive heart failure, compliance of 100% was achieved for four of the six months with an overall compliance of 94% being achieved.

Clearly, implementation of the test system in the unit if this health care facility provided a clear and dramatic improvement to the overall quality and efficacy of the care provided to patients. In addition, this system implementation has also resulted in the reduction of the average cost per patient stay and an improvement to the overall sense of patient satisfaction with the care provided.

A system according to the present disclosure may be incorporated into an existing operational and/or physical structure or a new operational or physical structure may be adopted within which to operate such a system. A facility or organization may implement the above-described approach to collaborative patient care as a method within an existing operational and/or physical structure or may adapt a new operational or physical structure within which to implement such a method.

What is claimed is:

1. A method of executing a patient care plan for a patient being treated at a health care facility, the method comprising:

providing an electronic medium and an associated electronic processor;

developing the patient care plan including a plurality of sequential phases of care, the phases of care including at least an intake phase, a care phase and a discharge phase, the phases of care being established when the patient is first diagnosed at the health care facility and the phases corresponding to the course of treatment indicated by the first diagnosis, wherein each of the phases including a plurality of actions and care objectives relating the treatment of the patient, and wherein the patient care plan is developed jointly by a plurality of health care providers including at least a physician, a pharmacist and a nurse;

recording the patient care plan in the electronic medium utilizing the electronic processor;

defining a tollgate associated with each of the phases, the tollgate listing all of the actions and care objectives associated with the planned treatment of the patient during the corresponding phase and addressing the tollgate requires that the status of each of the actions and care objectives of the corresponding phase be determined, wherein each of the actions and care objectives listed with the tollgate associated with a particular phase must be addressed before the next sequential phase of the patient care plan may begin;

recording the actions and care objectives of each tollgate in the electronic medium utilizing the electronic processor;

executing the actions and care objectives of the first phase of the patient care plan;

determining that the actions and care objectives of the tollgate corresponding to the first phase of the patient care plan have been met;

recording the status of the actions and care objectives listed with the tollgate in the electronic medium utilizing the electronic processor and altering a status indicator to indicate whether the objectives of the tollgate have been met; and executing the actions and care objectives of the next sequential phase of the patient care plan.

2. The method of executing the patient care plan of claim 1, further comprising the plurality of health care providers each diagnosing the patient simultaneously to develop the phases of the patient care plan.

3. The method of executing the patient care plan of claim 1, wherein one or more of the phases of the care plan may be altered from the plan if a second diagnosis of the patient indicates that a different course of treatment is indicated as compared to the first diagnosis.

4. The method of executing the patient care plan of claim 1, wherein the actions and care objectives for any sequential phase of the care plan may be altered if the status determined in the tollgate corresponding to an earlier phase indicates that change to the treatment of the patient is necessary and any actions and care objectives that are altered will be recorded in the electronic medium utilizing the electronic processor.

5. A method of executing a patient care plan, the method comprising:

providing a patient care team including at least a physician, a pharmacist and a nurse;

providing an electronic medium and an associated electronic processor;

the patient care team conducting an initial simultaneous examination of a patient at a health care facility and developing an initial diagnosis of the patient;

the patient care team creating the patient care plan based on the initial diagnosis, the patient care plan including a plurality of sequential patient care phases, the phases including at least an intake phase, a care phase and a discharge phase, wherein each phase includes a plurality of patient care actions and objectives to be accomplished in that phase, wherein the actions and objectives of each phase are recorded and stored in the electronic medium utilizing the electronic processor;

the patient care team creating a tollgate corresponding to each of the phases of the patient care plan and based on the actions and objectives of the corresponding phase, the tollgate including a plurality of objectives that must be satisfied before the patient care plan may transition to the next sequential phase of care;

recording the tollgates associated with the patient care plan in the electronic medium utilizing the electronic processor;

treating the patient based on the actions and objectives of the appropriate phase of the patient care plan;

determining whether the objectives of the tollgate corresponding to the current phase of the patient care plan have been satisfied, and if the objectives of the tollgate have not been satisfied, continuing treating the patient according to the current phase of the patient care plan;

recording the status of the actions and care objectives listed with the tollgate in the electronic medium utilizing the electronic processor and altering a status indicator to indicate whether the objectives of the tollgate have been satisfied;

if the objectives of the tollgate have not been satisfied, the patient care team determining if a change to the actions and objectives of the current phase of the patient care plan is necessary to permit the patient to progress to the next sequential phase of the patient care plan, and if a change is necessary to the actions and objectives of the current phase of the patient care plan, updating the electronic medium to reflect the changes;

if the objectives of the tollgate of the current phase of the patient care plan have been satisfied, transitioning the care of the patient to the next sequential phase of the patient care plan and recording the status of the actions and objectives of the current phase of the patient care plan the electronic medium utilizing the electronic processor; and treating the patient according the next sequential phase of the patient care plan until the objectives of the tollgate of the discharge phase have been satisfied and discharging the patient from the health care facility.

6. The method of claim 5, further comprising storing the patient care plan on a computer storage medium and storing the status of actions and objectives of each phase of the patient care plan as determined in addressing the corresponding tollgates on the computer storage medium.

7. The method of claim 5, further comprising modifying the patient care plan if the patient care team develops a second diagnosis during any of the phases of the patient care plan.

8. The method of claim 5, further comprising modification of the actions and objectives of a later sequential phase of the patient care plan based on the treatment of the patient during an earlier phase of the patient care plan.

* * * * *